United States Patent [19]

Asakawa et al.

[11] 4,081,526

[45] Mar. 28, 1978

[54] DENTIFRICE COMPOSITION

[75] Inventors: Toshiro Asakawa, Funabashi; Atsuo Ishida, Chiba; Shizuo Hayashi, Saitama, all of Japan

[73] Assignee: Kao Soap Co., Ltd., Tokyo, Japan

[21] Appl. No.: 734,131

[22] Filed: Oct. 20, 1976

[30] Foreign Application Priority Data

Nov. 7, 1975 Japan .................................. 50-133892

[51] Int. Cl.$^2$ ............................................... A61K 7/18
[52] U.S. Cl. ........................................................ 424/57
[58] Field of Search ..................................... 424/49–58

[56] References Cited

U.S. PATENT DOCUMENTS

| | | | |
|---|---|---|---|
| 2,069,157 | 1/1937 | Sahyun | 424/57 |
| 2,216,816 | 10/1940 | Kuever | 424/57 |
| 3,462,366 | 8/1969 | Luoma | 424/57 |
| 3,855,147 | 12/1974 | Granquist | 424/52 |

FOREIGN PATENT DOCUMENTS

| | | |
|---|---|---|
| 1,047,979 | 12/1953 | France. |
| 1,594,709 | 7/1970 | France. |
| 930,740 | 2/1948 | France. |
| 1,424,034 | 2/1976 | United Kingdom. |

*Primary Examiner*—Shep K. Rose
*Attorney, Agent, or Firm*—Blanchard, Flynn, Thiel, Boutell & Tanis

[57] ABSTRACT

A dentifrice composition comprising 0.5 to 5 wt.% of an alkali metal phosphate and 0.5 to 13 wt.% of monomorillonite having a composition (% by weight, calculated on an anhydrous basis) of 60.0 to 70.0% of $SiO_2$, 20.0 to 30.0% of $Al_2O_3$, 2.0 to 5.0% of MgO, 2.0 to 5.0% of $Na_2O$ and 0.0 to 2.0% of $Fe_2O_3$ or hectorite having a composition (% by weight, calculated on an anhydrous basis) of 50.0 to 65.0% of $SiO_2$, 20.0 to 30.0% of MgO, 2.5 to 5.0% of $Na_2O$, 0.6 to 2.0% of $Li_2O$ and 0.0 to 2.0% of $Fe_2O_3$.

7 Claims, No Drawings

DENTIFRICE COMPOSITION

CROSS REFERENCE TO RELATED APPLICATION

This application is related to Ser. No. 715,378, filed Aug. 18, 1976.

BACKGROUND OF THE INVENTION

1. Field of the Invention

The present invention relates to a dentifrice composition having an excellent property of removing plaque from teeth.

2. Description of the Prior Art

Plaque adhering on the surfaces of teeth, which has been formed by the action of microorganisms, polysaccharides, proteins and the like in the oral cavity, is a main cause of tooth decay, and removal of plaque is desired not only from the aesthetic viewpoint but also from the viewpoint of oral hygiene.

In general, plaque is removed from teeth by oral cleaning using a dentifrice and a tooth brush. According to this cleaning method, however, a sufficient cleaning effect cannot be obtained because the frequency of the cleaning operation is inevitably low.

Therefore, various attempts have heretofore been made to improve the physical polishing power of the polishing agents so as to enhance the cleaning effect of dentifrices. However, this method of improving the polishing power is still insufficient in the point that the teeth and gingivae are readily damaged and plaque is removed only from the parts that the tooth brush contacts.

SUMMARY OF THE INVENTION

We have discovered a dentifrice composition which has an excellent property of removing plaque from teeth chemically, without critically relying on the physical polishing method mentioned above, and we have now completed the present invention based on this finding.

More specifically, in accordance with the present invention, there is provided a dentifrice composition comprising (I) 0.5 to 5% of an alkali metal phosphate and (II) 0.5 to 13% of either (a) montmorillonite having a composition (% by weight, calculated on an anhydrous basis) of 60.0 to 70.0% of $SiO_2$, 20.0 to 30.0% of $Al_2O_3$, 2.0 to 5.0% of MgO, 2.0 to 5.0% of $Na_2O$ and 0.0 to 2.0% of $Fe_2O_3$, or (b) hectorite having a composition (% by weight, calculated on an anhydrous basis) of 50.0 to 65.0% of $SiO_2$, 20.0 to 30.0% of MgO, 2.5 to 5.0% of $Na_2O$, 0.6 to 2.0% of $Li_2O$ and 0.0 to 2.0% of $Fe_2O_3$.

The foregoing proportions of the above-listed ingredients of montmorillonite and hectorite are critical. The montmorillonite and hectorite can also contain additional components which do not alter the properties thereof for the purposes of the invention. For example montmorillonite commonly contains from zero to 6 wt.% of CaO and $K_2O$ and the presence of same does not alter the results. Likewise, hectorite can contain from zero to about 5 wt.% of $Al_2O_3$ and from about zero to about 13 wt.% of CaO plus $K_2O$ and the presence of same does not alter the results. These additional optional components are in the nature of inert substances that do not appreciably change the results.

The alkali metal phosphate that is used in the present invention includes sodium and potassium salts of orthophosphoric acid, metaphosphoric acid, pyrophosphoric acid and linear and cyclic polyphosphoric acids. Either acidic salts (that is, salts containing unreplaced hydrogen atoms from the acid) or normal salts (that is, a compound of a base and an acid that have completely neutralized each other), can be used in the present invention.

The composition of montmorillonite or hectorite is critically limited to those mentioned above and the reasons for this will now be described by reference to experimental results.

The effect of removing plaque was examined according to the following two methods.

It has been considered that sucrose is converted to dextran by bacteria in the oral cavity such as *Streptococcus mutans*, the thus-formed dextran has an adhesive property to tooth enamel and can hardly be removed and plaque is formed from such dextran. Tooth enamel is composed mainly of hydroxyapatite. In view of the foregoing two facts, the following method (1) was adopted.

Method (1)

A compound to be tested and hydroxyapatite powder are added to an aqueous solution of dextran, and the effect of preventing absorption of dextran into the hydroxyapatite is examined with respect to each test compound.

The following method (2) was adopted for evaluating the physical cleaning effect.

Method (2)

Artificial dental plaque is applied to ivory, and the ivory is brushed under prescribed conditions by using a dentifrice containing a compound to be tested. The removal effect is examined by a color difference metal after dyeing with a neutral scarlet dye.

Practical test procedures will now be described.

Method (1)

Experiments were carried out to determine the effects of montmorillonites and hectorites having the compositions indicated in Table 1 given below for preventing adhesion of dextran to hydroxyapatite powder.

Experimental Procedures

An additive to be tested was added to an aqueous solution of 15 mg of dextran in 10 ml of water so that a prescribed additive concentration was attained, and 1 g of hydroxyapatite powder was added to the aqueous solution. The mixture was agitated at room temperature for 30 minutes by a mini-stirrer, and then, the mixture was subjected to centrifugal separation for 5 minutes at 11,000 rpm. The supernatant liquid was diluted and the amount of non-adsorbed dextran was determined.

Determination (phenol-sulfuric acid method)

1.0 ml of a solution to be tested was charged in a test tube, and 1.0 ml of a 5% aqueous solution of phenol was added and the mixture was agitated so as to become homogeneous. Then, 0.5 ml of concentrated sulfuric acid was added to the mixture and reaction was conducted under agitation. The reaction mixture was allowed to stand still for 10 minutes and then was cooled with water. The absorbance at 489 m$\mu$ was measured, and a determination was conducted based on a calibration curve obtained by treating an aqueous solution of a known amount of dextran in the same manner as described above.

The adsorption preventing effect is expressed in terms of the value obtained by subtracting the absorption (%) of dextran to hydroxyapatite from 100. The results are shown in Table 2.

Table 1

Compositions of Montmorillonite and Hectorite Tested (% by weight, calculated on an anhydrous basis)

| Component | Montmorillonite | | | | | | Hectorite | | |
|---|---|---|---|---|---|---|---|---|---|
| | A (Invention) | B | C | D | E | F (Invention) | G | H | I |
| | | ←All controls→ | | | | | ←all controls→ | | |
| SiO$_2$ | 64.7 | 61.3 | 69.7 | 51.1 | 84.2 | 59.3 | 56.2 | 44.3 | 76.7 |
| Al$_2$O$_3$ | 25.0 | 24.5 | 16.7 | 31.9 | 5.4 | 1.4 | 3.4 | 1.0 | 0.9 |
| MgO | 3.9 | 1.5 | 2.1 | 6.4 | 0.9 | 26.2 | 23.2 | 34.2 | 5.4 |
| Na$_2$O | 3.3 | 1.4 | 2.1 | 5.3 | 1.2 | 3.5 | 0.8 | 1.0 | 0.9 |
| Fe$_2$O$_3$ | 1.8 | 4.3 | 3.9 | 3.2 | 4.4 | 0.5 | 3.3 | 5.6 | 3.2 |
| CaO | 0.8 | 3.9 | 3.9 | 1.2 | 3.1 | 7.8 | 10.0 | 12.2 | 11.0 |
| K$_2$O | 0.1 | 2.8 | 1.1 | 0.9 | 0.7 | 0.1 | 2.5 | 1.0 | 1.6 |
| Li$_2$O | 0.0 | 0.0 | 0.0 | 0.0 | 0.0 | 1.3 | 0.4 | 0.2 | 0.3 |

Table 2

| Additive Substance | Dextran Absorption Ratio (%) | Adsorption Preventing Effect |
|---|---|---|
| disodium hydrogenphosphate (control) | 61 | 39 |
| monosodium hydrogenphosphate (control) | 69 | 31 |
| sodium pyrophosphate (control) | 65 | 35 |
| sodium hexametaphosphate (control) | 70 | 30 |
| disodium hydrogenphosphate + montmorillonite A (Invention) | 39 | 61 |
| monosodium hydrogenphosphate + montmorillonite A (Invention) | 45 | 55 |
| sodium pyrophosphate + montmorillonite A (Invention) | 42 | 58 |
| sodium hexametaphosphate + montmorillonite A (Invention) | 47 | 53 |
| disodium hydrogenphosphate + montmorillonite B (control) | 53 | 47 |
| disodium hydrogenophosphate + montmorillonite C (control) | 55 | 45 |
| disodium hydrogenphosphate + montmorillonite D (control) | 58 | 42 |
| disodium hydrogenphosphate + montmorillonite E (control) | 60 | 40 |
| monosodium hydrogenphosphate + hectorite F (invention) | 42 | 58 |
| monosodium hydrogenphosphate + hectorite G (control) | 53 | 47 |
| monosodium hydrogenphosphate + hectorite H (control) | 57 | 43 |
| monosodium hydrogenphosphate + hectorite I (control) | 60 | 40 |
| montmorillonite A | 85 | 15 |
| hectorite F | 89 | 11 |

Amount Added:

| | |
|---|---|
| Disodium hydrogenphosphate, monosodium hydrogenphosphate, sodium pyrophosphate or sodium hexametaphosphate | 2.0 wt.% |
| Montmorillonite or hectorite | 5.0 wt.% |

From the results shown in Table 2, it is seen that each of disodium hydrogenphosphate, monosodium hydrogenphosphate, sodium pyrophosphate, sodium hexametaphosphate, montmorillonite A and hectorite F has an effect of preventing adhesion of dextran into hydroxyapatite. It is also seen that when an alkali metal phosphate such as disodium hydrogenphosphate is combined with montmorillonite A or hectorite F, a synergistic effect is attained and the effect of preventing adhesion of dextran to hydroxyapatite is remarkably enhanced. However, this synergistic effect is not attained when an alkali metal phosphate is combined with montmorillonite B, C, D or E or hectorite G, H or I.

Method (2) for Removal of Dental Plaque by Brushing Ivory: Experimental Procedures:

An artificial dental plaque (comprising 3.0 wt.% of bouillon, 0.3 wt.% of mucin, 0.3 to 5.0 wt.% of sugar, water and one platinum loopful of *Streptococcus mitis*) was applied to ivory. The contaminated ivory was washed in water, dried and dyed with a neutral scarlet dye, followed by washing and drying. Then, the L, a and b values were measured by a color difference meter (according to JIS Z 8701 and Z 8722). Then, the ivory was polished under the conditions indicated below, and it was then again dyed with the neutral scarlet dye. Then, values L', a' and b' were measured and the degree of contamination was evaluated based on ΔE calculated according to the following formula:

$$\Delta E = \sqrt{(L-L')^2 + (a-a')^2 + (b-b')^2}$$

A higher ΔE value signifies a higher removal effect.

Polishing Conditions:
  Dentifrice: 50 ml of 30% slurry
  Polishing force: 100 g
  Polishing frequency: 20 times (in 13 seconds)
Composition of Control Dental Cream:

| | |
|---|---|
| Dicalcium phosphate dihydrate | 45.0 parts by weight |
| Sorbitol | 2.0 parts by weight |
| Sodium lauryl sulfate | 2.0 parts by weight |
| Sodium carboxymethyl cellulose | 1.0 parts by weight |
| Antiseptic, flavoring agent and perfume | minor amounts |
| Water | balance |

-continued

| Total | 100 parts by weight |
|---|---|

Other dentifrice compositions were prepared by adding an alkali metal phosphate and montmorillonite or hectorite as indicated in Table 3 given hereinafter.

The results of the determination of the dental plaque removal effect (ΔE) are shown in Table 3.

The above test was conducted twice, namely just after the preparation of the dentifrice and after 6 months' storage.

| Amount Added: | |
|---|---|
| Alkali metal phosphate | 2.0 wt.% of the control dental cream |
| Montmorillonite or hectorite | 5.0 wt.% |

The term "reduction ratio" is calculated from the formula $$\frac{\Delta E_{initial} - \Delta E_{after\ storage}}{\Delta E_{initial}} \times 100$$

No substantial effect can be attained by the addition of montmorillonite B, C, D or E or hectorite G, H or I, alone, and even if they are used in combination with the alkali metal phosphate, the synergistic effect is low and the effect is reduced with the passage of time.

In view of the foregoing experimental results, it has been found that in order for montmorillonite and hectorite to show a high dental plaque removing effect which is scarcely reduced even with the passage of time, when they are used in combination with an alkali metal phosphate, they must have the following composition:

Montmorillonite (% by weight, calculated on an anhydrous basis):
$SiO_2$: 60.0 to 70.0%
$Al_2O_3$: 20.0 to 30.0%
$MgO$: 2.0 to 5.0%
$Na_2O$: 2.0 to 5.0%
$Fe_2O_3$: 0.0 to 2.0%

Hectorite (% by weight, calculated on an anhydrous basis):
$SiO_2$: 50.0 to 65.0%
$MgO$: 20.0 to 30.0%
$Na_2O$: 2.5 to 5.0%

Table 3

| Additive | Removal Effect (ΔE) just after preparation | after 6 months' storage | Reduction Ratio (%) | |
|---|---|---|---|---|
| disodium hydrogenphosphate | 20.7 | 13.0 | 37.2 | |
| monosodium hydrogenphosphate | 17.2 | 12.0 | 30.2 | |
| sodium pyrophosphate | 18.5 | 12.2 | 34.1 | |
| sodium hexametaphosphate | 18.0 | 12.1 | 32.8 | |
| montmorillonite A | 16.4 | 17.5 | | |
| montmorillonite B | 14.9 | 14.7 | | |
| montmorillonite C | 14.4 | 14.3 | | |
| montmorillonite D | 11.3 | 11.2 | | |
| montmorillonite E | 11.1 | 11.1 | | |
| hectorite F | 16.1 | 16.2 | | |
| hectorite G | 12.3 | 12.1 | | |
| hectorite H | 11.9 | 11.7 | | |
| hectorite I | 11.0 | 11.1 | | |
| disodium hydrogenphosphate + montmorillonite A | 30.1 | 28.3 | 6.0 | (invention) |
| disodium hydrogenphosphate + montmorillonite B | 25.5 | 21.0 | 17.6 | |
| disodium hydrogenphosphate + montmorillonite C | 25.2 | 20.4 | 19.0 | |
| disodium hydrogenphosphate + montmorillonite D | 22.3 | 17.0 | 23.8 | |
| disodium hydrogenphosphate + montmorillonite E | 22.2 | 15.1 | 32.0 | |
| disodium hydrogenphosphate + hectorite F | 30.3 | 29.4 | 3.0 | (invention) |
| disodium hydrogenphosphate + hectorite G | 25.1 | 20.9 | 16.7 | |
| disodium hydrogenphosphate + hectorite H | 23.5 | 18.7 | 20.4 | |
| disodium hydrogenphosphate + hectorite I | 23.1 | 18.1 | 21.6 | |
| monosodium hydrogenphosphate + montmorillonite A | 27.1 | 26.0 | 4.1 | (invention) |
| monosodium hydrogenphosphate + hectorite F | 26.9 | 25.9 | 3.7 | (invention) |
| sodium pyrophosphate + montmorillonite A | 28.4 | 27.2 | 4.2 | (invention) |
| sodium pyrophosphate + hectorite F | 28.0 | 26.9 | 3.9 | (invention) |
| sodium hexametaphosphate + montmorillonite A | 27.8 | 26.2 | 5.8 | (invention) |
| sodium hexametaphosphate + hectorite F | 27.4 | 26.0 | 5.1 | (invention) |
| control (no addition of alkali metal phosphate and montmorillonite) | 10.4 | 10.2 | | |

From the results shown in Table 3, it is seen that alkali metal phosphates such as disodium hydrogenphosphate, monosodium hydrogenphosphate, sodium pyrophosphate and sodium hexametaphosphate and montmorillonite and hectorite have a dental plaque removal effect, though the effect is very low, and that this effect is remarkably enhanced when an alkali metal phosphate is used in combination with montmorillonite A or hectorite F and this enhanced effect is maintained even if the dentifrice is stored for a long time.

The reason for this improved effect is considered to be that although the alkali metal phosphate reacts with dicalcium phosphate gradually with the passage of time, this reaction is reduced by the addition of montmorillonite A or hectorite F.

$Li_2O$: 0.6 to 2.0%
$Fe_2O_3$: 0.0 to 2.0%

The method for preparing montmorillonite or hectorite having the above specific composition is not particularly critical in the present invention. It is, however, preferred to collect a high-quality starting ore having low contents and impurities such as cristobalite, feldspar, mica and quartz from a bentonite layer, remove the impurities by water sieving, dry the purified ore, pulverize it and use the resulting powdery product.

If the amount of montmorillonite or hectorite having the above specific composition that is to be added to a dentifrice is too small, the intended dental plaque removal effect cannot be attained, but if the amount is too large, the resulting dentifrice is too hard and a pasty composition cannot be obtained. Accordingly, it is preferred that the amount of montmorillonite or hectorite be 0.5 to 13%, especially 1 to 6%.

If the amount of the alkali metal phosphate added to a dentifrice is too small, the intended tooth impurity removal effect cannot be obtained but if the amount is too large, the electrolyte concentration becomes too high and it is impossible to keep the composition as a stable paste form, with the result being that an acceptable dentifrice cannot be prepared. Accordingly, it is preferred that the amount of the alkali metal phosphate be 0.5 to 5.0%, preferably 1 to 3%.

The dentifrice composition according to this invention can contain conventional amounts of other conventional dentifrice base ingredients, comprising a polishing agent, a swelling agent and a foaming agent. The polishing agent can be calcium phosphate dibasic dihydrate, calcium carbonate, calcium pyrophosphate, aluminum hydroxide, silica, kaolin or alumina. The amount of the polishing agent used in the dentifrice composition is from 5 to 70 wt.%, preferably 15 to 60%, based on the total weight of the composition. The swelling agent can be glycerin, sorbitol, propylene glycol or sodium polycarboxylate. The amount of the swelling agent is from 5 to 50 weight %, preferably 10 to 30%. The foaming agent can be an organic surfactant such as sodium alkyl sulfate having 8 to 20 carbon atoms, sodium N-lauroyl sarcosinate, sodium monoglyceride sulfate, sucrose ester, sodium alkylsulfoacetates, sodium sulfocolaurate or alkanesulfonates. The amount of the foaming agent is from 0.3 to 5.0 wt.%.

The dentifrice composition according to this invention may also include other conventional additives in addition to the critical ingredients, namely, an alkali metal phosphate and montmorillonite or hectorite. For example there can be used 0.3 to 5.0 wt.% of a binder such as sodium carboxymethyl cellulose, hydroxyethyl cellulose, sodium carboxymethyl hydroxyethyl cellulose, methyl cellulose, carrageen, sodium alginate, xanthan gum, hypnea, guar gum, locust bean gum, gum tragacanth and polyvinyl alcohol; 0.01 to 10.0 weight % of a sweetening agent such as sodium saccharin; and 0.01 to 1.0 weight % of a preservative such as sodium benzoate and ethyl p-hydroxybenzoate. There may be further included therein various pharmaceutical agents and perfumes according to need.

It is preferred to adopt the following procedures when montmorillonite or hectorite having the above-mentioned specific composition is used for the preparation of a dentifrice composition.

Powdery starting materials are added to water, and the mixture is agitated at an agitation speed of at least 100 rpm thereby to effect dispersion and swelling. The agitation need not be carried out at an especially elevated temperature, but if the agitation is conducted at about 50° to about 60° C, the viscosity is promptly increased and a higher viscosity can be obtained. Alternately, montmorillonite or hectorite is dispersed in an aqueous solution of sorbitol or glycerin containing sodium saccharin and an antiseptic or the like in the state of being dissolved homogeneously therein and the dispersion is agitated at an agitation rate of at least 100 rpm to effect swelling. Then, a base, a medicinal agent and the like are added to the thus-formed composition, followed by agitation, and finally, a foaming agent, a perfume and the like are added to the composition and the composition is defoamed and agitated to obtain a dentifrice composition. According to this invention, an alkali metal phosphate may be added at any time of the procedure for preparing a composition, but it is preferred to be added as a medicinal agent.

The present invention will now be described in detail by reference to the following examples, in which all references to "parts" mean parts by weight.

EXAMPLE 1

| | |
|---|---|
| Dicalcium phosphate dihydrate | 43 parts |
| Glycerin | 13 parts |
| Sorbitol | 10 parts |
| Sodium carboxymethyl cellulose | 1.0 part |
| Sodium lauryl sulfate | 1.6 parts |
| Montmorillonite (A, Table 1) | 2.0 parts |
| Disodium hydrogenphosphate | 1.5 parts |
| Sodium benzoate | 0.2 part |
| Flavoring agent and perfume | minor amounts |
| Water | balance |
| Total | 100 parts |

Sodium carboxymethyl cellulose was dispersed into glycerin, and sorbitol and water were added to the dispersion and the mixture was agitated until a homogeneous solution was obtained. Then, sodium benzoate, the flavoring agent and montmorillonite were added to the thus-obtained transparent viscous solution and dissolved homogeneously in the solution. Then, dicalcium phosphate dihydrate was added and the mixture was sufficiently kneaded to obtain a homogeneous paste. The paste was defoamed and sodium lauryl sulfate and the perfume were added to the paste. Then, the mixture was well blended and defoamed to obtain a dentifrice.

EXAMPLE 2

| | |
|---|---|
| Dicalcium phosphate dihydrate | 40 parts |
| Glycerin | 20 parts |
| Sodium carboxymethyl cellulose | 0.3 part |
| Sodium lauryl sulfate | 1.9 parts |
| Monosodium hydrogenphosphate | 3.0 parts |
| Sodium benzoate | 0.2 part |
| Flavoring agent and perfume | minor amounts |
| Hectorite (F in Table 1) | 5.0 parts |
| Water | balance |
| Total | 100 parts |

A dentifrice was prepared from the above components in the same manner as in Example 1.

EXAMPLE 3

| | |
|---|---|
| Dicalcium phosphate dihydrate | 48 parts |
| Propylene glycol | 5 parts |
| Sorbitol | 19 parts |
| Sodium carboxymethyl cellulose | 1.7 parts |
| Montmorillonite (A in Table 1) | 5.0 parts |
| Disodium hydrogenphosphate | 2.5 parts |
| Sodium benzoate | 0.2 part |
| Flavoring agent and perfume | minor amounts |
| Water | balance |
| Total | 100 parts |

Sodium carboxymethyl cellulose was dispersed in propylene glycol, and sorbitol and water were added to the dispersion and the mixture was agitated until a homogeneous solution was obtained. Sodium benzoate, the flavoring agent and montmorillonite were homogeneously dissolved in the thus-formed transparent viscous solution. Then, dicalcium phosphate dihydrate was added to the solution and the mixture was sufficiently kneaded to form a homogeneous paste. The paste was defoamed and sodium lauryl sulfate and the perfume were added to the paste. The mixture was well blended and defoamed to obtain a dentifrice.

EXAMPLE 4

| | |
|---|---|
| Dicalcium phosphate dihydrate | 40 parts |
| Glycerin | 10 parts |
| Sorbitol | 10 parts |
| Sodium lauryl sulfate | 1.8 parts |
| Sodium benzoate | 0.2 part |
| Flavoring agent and perfume | minor amounts |
| Montmorillonite (A in Table 1) | 7.0 parts |
| Water | balance |
| Total | 100 parts |

Sodium benzoate and the flavoring agent were uniformly dissolved in water, glycerin and sorbitol, and montmorillonite was added to the solution and the mixture was agitated until a homogeneous mixture was formed. Then, dicalcium phosphate dihydrate was added to the mixture and the resulting mixture was sufficiently kneaded to form a paste. The paste was defoamed, and sodium lauryl sulfate and the perfume were added to the paste. The mixture was kneaded and defoamed to obtain a dentifrice.

The embodiments of the invention in which an exclusive property or privilege is claimed are defined as follows:

1. A dentifrice composition containing from 0.5 to 5.0 weight percent of an alkali metal phosphate, and from 0.5 to 13 percent by weight of a substance selected from the group consisting of
   (a) montmorillonite having the composition, in terms of percent by weight, calculated on an anhydrous basis,

| | |
|---|---|
| $SiO_2$ | 60.0 to 70.0 |
| MgO | 2.0 to 5.0 |
| $Fe_2O_3$ | zero to 2.0 |
| $Al_2O_3$ | 20.0 to 30.0 |
| $Na_2O$ | 2.0 to 5.0 | and
   (b) hectorite having the composition, in terms of percent by weight, calculated on an anhydrous basis,

| | |
|---|---|
| $SiO_2$ | 50.0 to 65.0 wt.% |
| $Na_2O$ | 2.5 to 5.0 wt.% |
| $Fe_2O_3$ | zero to 2.0 wt.% |
| MgO | 20.0 to 30.0 wt.% |
| $Li_2O$ | 0.6 to 2.0. |

2. A dentifrice as claimed in claim 1 containing from 1 to 3 weight percent of said alkali metal phosphate, and from 1 to 6% by weight of said substance.

3. A dentifrice composition as claimed in claim 1 in which the balance of said composition consists essentially of from 5 to 70 wt.% of a polishing agent, from 5 to 40 wt.% of a swelling agent, from 0.3 to 5 wt.% of a foaming agent and water.

4. A dentifrice composition according to claim 1, in which said alkali metal phosphate is selected from the group consisting of the acid and normal, sodium and potassium, salts of orthophosphoric acid, metaphosphoric acid, pyrophosphoric acid, linear polyphosphoric acids and cyclic polyphosphoric acids.

5. A dentifrice composition according to claim 1 in which said alkali metal phosphate is selected from the group consisting of disodium hydrogenphosphate, monosodium hydrogenphosphate, sodium pyrophosphate and sodium hexametaphosphate.

6. A dentifrice composition according to claim 5 in which said substance consists of said montmorillonite.

7. A dentifrice composition according to claim 5 in which said substance consists of said hectorite.

* * * * *